United States Patent
Horvath et al.

(10) Patent No.: US 11,045,639 B2
(45) Date of Patent: Jun. 29, 2021

(54) VENTRICULAR ASSIST DEVICE WITH PULSE AUGMENTATION AND AUTOMATIC REGURGITANT FLOW SHUTOFF

(71) Applicant: THE CLEVELAND CLINIC FOUNDATION, Cleveland, OH (US)

(72) Inventors: David J. Horvath, Cleveland, OH (US); Leonard A R. Golding, Cleveland, OH (US); Barry D. Kuban, Cleveland, OH (US); Kiyotaka Fukamachi, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 318 days.

(21) Appl. No.: 15/772,154

(22) PCT Filed: Oct. 28, 2016

(86) PCT No.: PCT/US2016/059275
§ 371 (c)(1),
(2) Date: Apr. 30, 2018

(87) PCT Pub. No.: WO2017/075322
PCT Pub. Date: May 4, 2017

(65) Prior Publication Data
US 2018/0311426 A1    Nov. 1, 2018

Related U.S. Application Data

(60) Provisional application No. 62/247,974, filed on Oct. 29, 2015, provisional application No. 62/327,073, filed on Apr. 25, 2016.

(51) Int. Cl.
*A61M 1/12*    (2006.01)
*A61M 60/148*    (2021.01)
(Continued)

(52) U.S. Cl.
CPC ........ *A61M 60/148* (2021.01); *A61M 60/205* (2021.01); *A61M 60/422* (2021.01); *A61M 60/833* (2021.01); *A61M 60/50* (2021.01)

(58) Field of Classification Search
CPC .... A61M 1/122; A61M 1/101; A61M 1/1031; A61M 1/1086; A61M 1/1015;
(Continued)

(56) References Cited

U.S. PATENT DOCUMENTS 5,324,177 A * 6/1994 Golding .................... F04D 1/04
                                                          415/900
8,608,798 B2 * 12/2013 Wampler ............... A61M 1/122
                                                          623/3.13
(Continued)

FOREIGN PATENT DOCUMENTS

WO    94/09274 A1    4/1994
WO    2011/069109 A2    6/2011

OTHER PUBLICATIONS

Aggarwal, Ashim, et al. "The development of aortic insufficiency in continuous-flow left ventricular assist device-supported patients." The Annals of thoracic surgery 95.2 (2013): 493-498.
(Continued)

*Primary Examiner* — Deborah L Malamud
(74) *Attorney, Agent, or Firm* — Tarolli, Sundheim, Covell & Tummino LLP

(57) ABSTRACT

A ventricular assist device includes a housing including a pumping chamber. A stator assembly is supported in the housing. The stator assembly includes a core having a length measured along a pump axis. A rotating assembly is rotatable relative to the stator assembly about the pump axis. The rotating assembly includes an impeller positioned in the pumping chamber and a rotor magnet. The rotating assembly is movable axially along the pump axis relative to the pump housing and the stator assembly. The rotating assembly (Continued)

includes a rotor magnet configured and arranged such that the magnetic attraction of the rotor magnet to the core urges the rotating assembly to move axially relative to the stator assembly such that a flow regulating portion of the rotating assembly engages with a corresponding portion of the housing to block flow through the pumping chamber when the pump is at rest.

22 Claims, 4 Drawing Sheets

(51) Int. Cl.
    *A61M 60/205* (2021.01)
    *A61M 60/422* (2021.01)
    *A61M 60/833* (2021.01)
    A61M 60/50 (2021.01)

(58) Field of Classification Search
    CPC .............. A61M 1/1036; A61M 1/1012; A61M 1/1017; A61M 2205/3334; A61M 1/12; A61M 2205/3317; A61M 1/10; A61M 1/1001; A61M 2025/1022; A61M 2205/103; Y10S 415/90
    See application file for complete search history.

(56) References Cited

U.S. PATENT DOCUMENTS

| | | |
|---|---|---|
| 2012/0328460 A1 | 12/2012 | Horvath et al. |
| 2014/0058190 A1* | 2/2014 | Gohean .............. A61M 1/1081 600/17 |

OTHER PUBLICATIONS

Ambrosy, Andrew P., et al. "The global health and economic burden of hospitalizations for heart failure: lessons learned from hospitalized heart failure registries." Journal of the American College of Cardiology 63.12 (2014): 1123-1133.
Bhamidipati, Castigliano M., et al. "Early thrombus in a HeartMate II left ventricular assist device: a potential cause of hemolysis and diagnostic dilemma." The Journal of thoracic and cardiovascular surgery 140.1 (2010): e7-e8.
Boyle, Andrew J., et al. "Pre-operative risk factors of bleeding and stroke during left ventricular assist device support: an analysis of more than 900 HeartMate II outpatients." Journal of the American College of Cardiology 63.9 (2014): 880-888.
Brisco, Meredith A., et al. "Prevalence and prognostic importance of changes in renal function after mechanical circulatory support." Circulation: Heart Failure 7.1 (2014): 68-75.
Cowger, Jennifer, et al. "The development of aortic insufficiency in left ventricular assist device-supported patients." Circulation: Heart Failure 3.6 (2010): 668-674.
Cowger, Jennifer, et al. "Comprehensive review and suggested strategies for the detection and management of aortic insufficiency in patients with a continuous-flow left ventricular assist device." The Journal of Heart and Lung Transplantation 34.2 (2015): 149-157.
Eckman, Peter M., and Ranjit John. "Bleeding and thrombosis in patients with continuous-flow ventricular assist devices." Circulation 125.24 (2012): 3038-3047.
Kalavrouziotis, Dimitri, et al. "Percutaneous lead dysfunction in the HeartMate II left ventricular assist device." The Annals of thoracic surgery 97.4 (2014): 1373-1378.
Kirklin, James K., et al. "Sixth Intermacs annual report: a 10,000-patient database." The Journal of Heart and Lung Transplantation 33.6 (2014): 555-564.
Kirklin, James K., et al. "Interagency Registry for Mechanically Assisted Circulatory Support (INTERMACS) analysis of pump thrombosis in the HeartMate II left ventricular assist device." The Journal of Heart and Lung Transplantation 33.1 (2014): 12-22.
Krabatsch, Thomas, et al. "Evaluation of the HeartWare HVAD centrifugal pump for right ventricular assistance in an in vitro model." Asaio Journal 57.3 (2011): 183-187.
Lampert, Brent C., et al. "Blood pressure control in continuous flow left ventricular assist devices: efficacy and impact on adverse events." The Annals of thoracic surgery 97.1 (2014): 139-146.
Moazami, Nader, et al. "Mechanical circulatory support for heart failure: past, present and a look at the future." Expert review of medical devices 10.1 (2013): 55-71.
Morgan, Jeffrey A., et al. "Stroke while on long-term left ventricular assist device support: incidence, outcome, and predictors." ASAIO journal 60.3 (2014): 284-289.
Morgan, Jeffrey A., et al. "Gastrointestinal bleeding with the HeartMate II left ventricular assist device." The Journal of Heart and Lung Transplantation 31.7 (2012): 715-718.
Muthiah, Kavitha, et al. "Thrombolysis for suspected intrapump thrombosis in patients with continuous flow centrifugal left ventricular assist device." Artificial organs 37.3 (2013): 313-318.
Soleimani, Behzad, et al. "Development of aortic insufficiency in patients supported with continuous flow left ventricular assist devices." Asaio Journal 58.4 (2012): 326-329.
Starling, Randall C., et al. "Unexpected abrupt increase in left ventricular assist device thrombosis." New England Journal of Medicine 370.1 (2014): 33-40.
Stulak, John M., et al. "Gastrointestinal bleeding and subsequent risk of thromboembolic events during support with a left ventricular assist device." The Journal of Heart and Lung Transplantation 33.1 (2014): 60-64.
Sunagawa, Gengo, et al. "In vitro hemodynamic characterization of HeartMate II at 6000 rpm: Implications for weaning and recovery." The Journal of thoracic and cardiovascular surgery 150.2 (2015): 343-348.
Sunagawa, Gengo, et al. "The contribution to hemodynamics even at very low pump speeds in the HVAD." The Annals of thoracic surgery 101.6 (2016): 2260-2264.
Wever-Pinzon, Omar, et al. "Pulsatility and the risk of nonsurgical bleeding in patients supported with the continuous-flow left ventricular assist device HeartMate II." Circulation: Heart Failure 6.3 (2013): 517-526.
PCT International Search Report and Written Opinion for corresponding International Application Serial No. PCT/US2016/059275, dated Jan. 25, 2017, pp. 1-11.

* cited by examiner

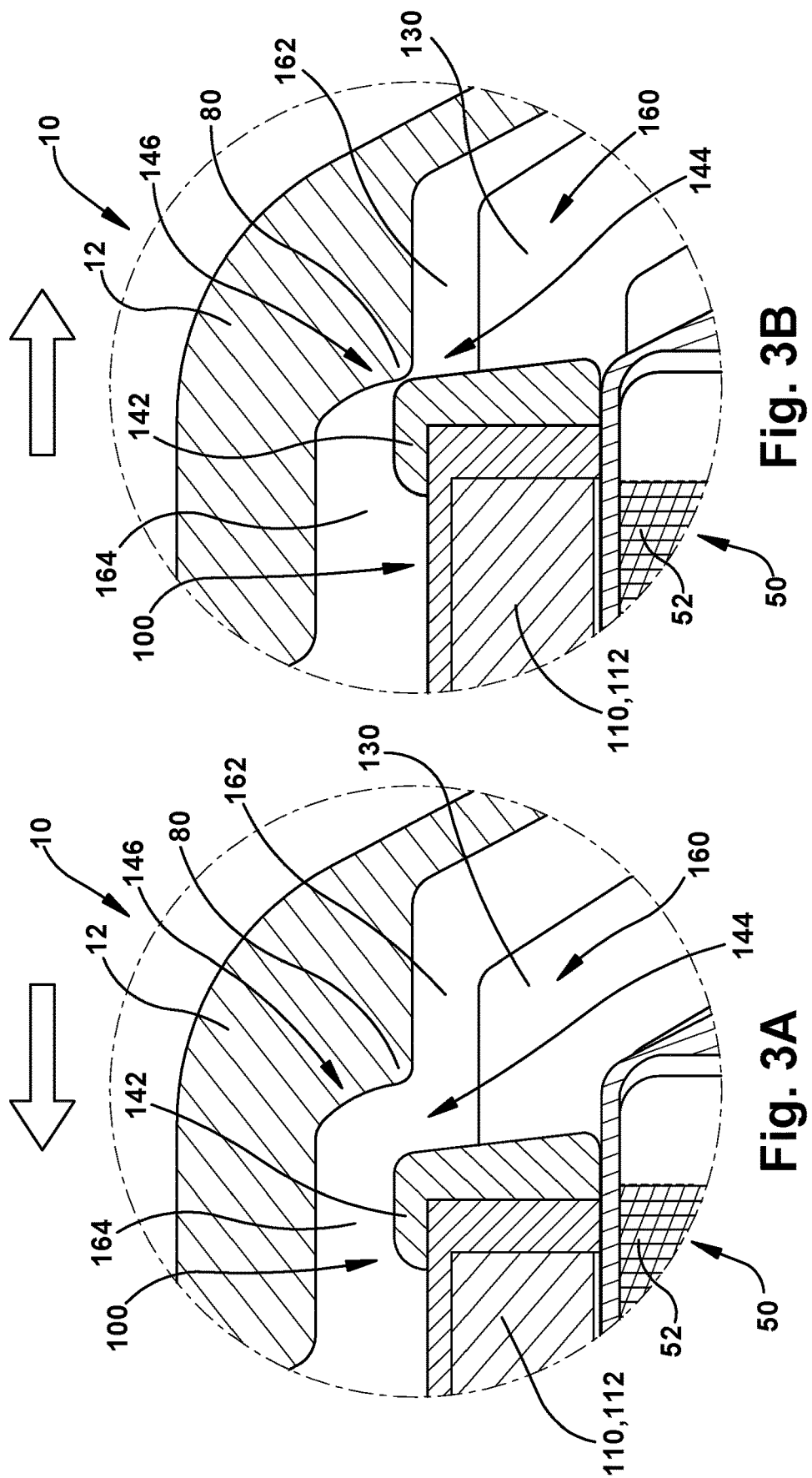

VENTRICULAR ASSIST DEVICE WITH PULSE AUGMENTATION AND AUTOMATIC REGURGITANT FLOW SHUTOFF

RELATED APPLICATIONS

This application is a 3.71 National Phase of PCT/US16/59275, filed on Oct. 28, 2016 which claims the benefit of U.S. Provisional Application Ser. No. 62/247,974, filed on Oct. 29, 2015 and U.S. Provisional Application Ser. No. 62/327,073, filed on Apr. 25, 2016. The disclosures of these applications are hereby incorporated by reference in their entireties.

GOVERNMENT FUNDING

This invention was made with government support under HL074896, HL089052, HL096619 and HV058159 awarded by the National Institutes of Health. The government has certain rights in the invention.

FIELD OF THE INVENTION

The invention relates to ventricular assist devices for supplementing the pumping action of the right or left ventricle of a patient's heart. More specifically, the invention relates to a ventricular assist device with enhanced pulsatility features and features for automatic shutoff to help prevent regurgitant flow.

BACKGROUND

Increasingly, continuous-flow rotary pumps are replacing volume-displacement pulsatile flow pumps for the treatment of severe heart failure. Continuous-flow ventricular assist devices (VADs) are favored because of their simplicity, increased mechanical reliability, improved durability, smaller size, and overall improved patient outcomes. Current continuous-flow rotary pump devices can suffer from some clinical limitations:

Reduced arterial pulsatility.
Threat of pump thrombosis or hemolysis.
Risk of syncope and death from backflow during pump stoppage (induced by accident or intentionally, e.g., for controller exchange or assessment of patient condition or weanability).
Inability to noninvasively evaluate weanability by pump-off test.
Narrow operating specifications, meaning there is no universal device without pivot bearings for use as both left and right VAD (LVAD and RVAD, respectively).
Potential inlet obstruction from suctioning of left ventricular wall into the inlet.

SUMMARY

The invention relates to a ventricular assist device (VAD) for helping to overcome the limitations with current continuous-flow VADs. The VAD is a brushless DC motor pump that has a continuous-flow design with several features or aspects that will improve the outcomes of patients with severe heart failure, providing safe and effective cardiac support as a bridge to transplant and/or destination therapy.

According to one aspect, the VAD can include a rotating assembly, including an impeller and a motor rotor, that has a pre-defined degree of freedom to move axially along its axis of rotation within the pumping chamber. Hydrodynamic pumping forces cause the rotating assembly to lift-off and levitate or become suspended during use. In this suspended condition, the rotating assembly responds inherently and automatically to differential pressures across the pump and variations in pump speed. Advantageously, the rotating assembly can respond to cyclic changes in differential pressures that occur in response to the native activity of the ventricle that the VAD is assisting.

According to another aspect, the rotating assembly can be positioned in a pumping chamber that is configured so that the geometry of the pump changes in response to the axial position of the rotating assembly. This axial movement or "shuttling" of the impeller within the pumping chamber gives the VAD a variable geometry configuration. Further, the VAD can deliver a signal that can be calibrated with pumped flow, allowing it to act as a virtual flow meter.

According to another aspect, the VAD can help maintain physiological pulsatility in a patient on VAD support. The rotor position can move axially back and forth passively during the cardiac cycle to have more flow during systole and less flow during diastole, increasing the pulsatility of the pump flow. This helps amplify the native pressure and flow pulsatility by dynamically coupling with the native ventricle, and can also use modulating speed to further enhance pulsatility. Reduced pulsatility from conventional continuous-flow VADs has been found to increase complications of gastrointestinal bleeding and aortic valve regurgitation.

According to another aspect, the VAD can help reduce the risk of pump thrombosis or hemolysis by implementing passive suspension of the rotating assembly. This design can eliminate pivot bearings, guide vanes, and mechanical structures where blood can clot and collect or which can damage the blood through contact.

According to another aspect, the VAD can help prevent backflow by enabling automatic flow shutoff in the event of pump stoppage, such as upon the occurrence of an interruption of power. This can inhibit blood from reverse shunting across the pump, which is dangerous because blood goes backward from the aorta to the left ventricle (in the case of an LVAD) or from the pulmonary artery to the right ventricle (in the case of an RVAD), causing severe heart failure. This fail safe feature minimizes the likelihood of loss of consciousness and death due to pump stoppage and blood backflow across the pump.

According to another aspect, the VAD can help avoid suction events by automatically attenuating pump output through automatic closure of a flow regulating aperture if ventricular walls begin to restrict the pump inlet. Due to the shuttling of the rotating assembly, the pump impeller moves within the pumping chamber to close the flow regulating aperture which causes the pump output to decrease automatically, reducing pump suction, in response to inlet restrictions.

According to another aspect, the VAD can help enable non-invasive evaluation of the ability to wean the patient off the VAD. The same automatic flow shutoff feature that prevents backflow flow can also allow the VAD to be slowed or stopped in order to evaluate the ability of the patient's heart to function on its own. This can help avoid the need to perform invasive procedures, such as occluding the VAD outflow graft, in order to test whether the patient can be weaned from the device. More importantly, this allows a pump-off test for weaning the patient off ventricular assist without any issues of blood regurgitation. The practice of running the assist pump at low speed to judge the capability of weaning is problematic due to blood regurgitation that occurs at low speed operation.

According to another aspect, the VAD can help provide wide operating specifications, which can enable use of the VAD as either an LVAD or RVAD, with the same pump hardware and electronics. The VAD can be used as an LVAD or RVAD without modification. RVADs have not been developed for clinical use because of the lesser market compared to LVADs. Using conventional LVADs for an RVAD application, typically by clamping the outlet to reduce output, has been clinically problematic. The VAD, being designed to handle both applications, addresses these clinical and economic issues.

The pump configuration of the proposed design implements self-regulating features to allow the impeller to move in and out of a housing cavity in response to system pressures, thereby opening and closing a flow regulating aperture at the impeller discharge. A weak magnet force acts on the rotating assembly to close the flow regulating aperture, while the hydraulic forces created by pump rotation act in the opposite direction to open it. So, if the pump stops rotation, the hydraulic forces disappear and the axial magnet force causes the flow regulating aperture to automatically close, preventing backflow of blood across the pump.

According to one aspect, a ventricular assist device having a centrifugal pump configuration includes a housing including a pumping chamber. A stator assembly is supported in the housing and has a length measured along a pump axis. A rotating assembly is supported in the housing and rotatable relative to the stator assembly about the pump axis. The rotating assembly includes an impeller positioned in the pumping chamber and a rotor magnet. The rotating assembly is configured to engage the housing to block flow through the pumping chamber when the pump is at rest.

According to another aspect, alone or in combination with one or more of the aspects described herein, the rotating assembly can be movable axially along the pump axis relative to the pump housing and the stator assembly. The rotating assembly and stator assembly can be configured and arranged such that the magnetic attraction of the rotor magnet to the core urges the rotating assembly to move axially relative to the stator assembly such that flow through the pumping chamber is blocked when a flow regulating portion of the rotating assembly engages with a corresponding portion of the housing.

According to another aspect, alone or in combination with one or more of the aspects described herein, the rotor magnet can include a first portion having a comparatively strong magnetic attraction to the core and that does not influence the axial position of the rotating assembly relative to the stator. The rotor magnet can also include a second portion having a comparatively weak magnetic attraction to the core and that does influence the axial position of the rotating assembly relative to the stator.

According to another aspect, alone or in combination with one or more of the aspects described herein, the rotor magnet can include a first portion and a second portion. The rotating assembly and stator assembly can be configured and arranged such that the first portion of the rotor magnet is positioned between axial ends of the core during pump operation, and the second portion of the rotor magnet is at least partially positioned axially beyond an axial end of the core regardless of the axial position of the rotating assembly relative to the stator assembly.

According to another aspect, alone or in combination with one or more of the aspects described herein, the rotor magnet can be a hollow cylindrical structure. The first portion of the rotor magnet can have a first thickness and the second portion of the rotor magnet can have a second thickness that is less than the first thickness. The first thickness and second thickness can be measured between respective cylindrical inner and outer walls of the first and second portions of the rotor magnet. The inner wall of the second portion of the rotor magnet can be spaced radially farther from the core than the first portion of the rotor magnet.

According to another aspect, alone or in combination with one or more of the aspects described herein, the ventricular assist device can include a flow regulating aperture defined by the pump housing and the rotating assembly. The flow regulating aperture can have a size that varies with the axial position of the rotating assembly relative to the stator assembly. The flow regulating aperture can be defined between the flow regulating portion of the rotating assembly and the corresponding portion of the housing. The flow regulating portion of the rotating assembly can include an annular rim adjacent the impeller.

According to another aspect, alone or in combination with one or more of the aspects described herein, the impeller can be configured to move fluid from a pump inlet through the pumping chamber to a pump outlet. The flow regulating aperture can be configured to regulate flow through the pumping chamber.

According to another aspect, alone or in combination with one or more of the aspects described herein, the rotating assembly can be configured such that hydrodynamic pumping forces created by the impeller urge the rotating assembly to move axially relative to the stator assembly in a direction that increases the size of the flow regulating aperture.

According to another aspect, alone or in combination with one or more of the aspects described herein, the impeller and pumping chamber can be configured so that the pump geometry changes in response to the axial position of the of the impeller in the pumping chamber so that pump output increases in response to increases in the size of the flow regulating aperture.

According to another aspect, alone or in combination with one or more of the aspects described herein, the rotating assembly can be configured such that hydrodynamic pumping forces created by the impeller urge the rotating assembly to move axially relative to the stator assembly in a direction that is opposite the axial direction that the rotor magnet urges the rotating assembly to move.

According to another aspect, alone or in combination with one or more of the aspects described herein, the impeller and pumping chamber can be configured so that the pump geometry changes in response to the axial position of the of the impeller in the pumping chamber so that pump output varies in response to the axial position of the rotating assembly.

According to another aspect, alone or in combination with one or more of the aspects described herein, the axial position of the rotating assembly can change in response to differential pressures across the pump so that the axial position of the rotating assembly follows the cyclic pressure changes produced by the native ventricle for which it is implemented to assist. The pump output is configured to increase in response to systole and decrease in response to diastole.

According to another aspect, alone or in combination with one or more of the aspects described herein, the ventricular assist device can include a sensor for providing a signal indicative of the axial position of the rotating assembly relative to the housing and a controller for determining via calibration the hemodynamic environment of the pump in response to the sensed axial position of the rotor assembly and motor operating parameters for the ventricular assist device. The hemodynamic environment of the pump determined by the controller via calibration can be characterized by at least one of the following parameters:

beat rate determined as a function of rotor axial position frequency.

pump mean flow determined as a function of speed, power, and rotor axial position.

pump flow pulse amplitude determined as a function of speed, power pulse, and rotor axial position pulse.

pump mean pressure rise determined as a function of speed, power, and rotor axial position.

pump pressure pulse amplitude determined as a function of speed, power pulse, and rotor axial position pulse.

pump mean work determined as a function of flow multiplied by pressure rise.

pump pulse work determined as a function of beat rate, flow pulse, and pressure pulse.

aortic valve opening/closing determined as a function of an identifying feature in the rotor axial position wave form or via a power versus position hysteresis loop.

suction recognition determined as a function of an identifying feature in rotor axial position wave form or via a power versus position hysteresis loop.

relative change in pulsatility since baseline determined as a function of a comparison with the history of hemodynamic parameters.

According to another aspect, alone or in combination with one or more of the aspects described herein, the pump can be configured to block back flow through the pumping chamber in response to a loss of electrical power to the pump.

According to another aspect, a ventricular assist device having a centrifugal pump configuration can include a housing comprising a pumping chamber. A stator assembly can be supported in the housing. The stator assembly can include a stator core. A rotating assembly can be supported in the housing. The rotating assembly can be rotatable relative to the stator assembly about the pump axis and movable relative to the stator assembly along the pump axis. The rotating assembly can include an impeller positioned in the pumping chamber and a rotor magnet. The magnetic attraction of the rotor magnet to the core can urge the rotating assembly to move axially in a first direction, and hydrodynamic pumping forces created by the impeller during pump operation can urge the rotating assembly to move axially in a second direction, opposite the first direction. The pumping chamber and the impeller can be configured so that pump output decreases when the rotating assembly moves axially in the first direction and increases when the rotating assembly moves axially in the first direction. The axial position of the rotating assembly can respond inherently to differential pressures across the pump and variations in pump speed by moving to an axial position where the hydrodynamic forces produced by impeller rotation balance with magnetic forces urging the rotating assembly in the opposite direction.

According to another aspect, alone or in combination with one or more of the aspects described herein, the magnetic attraction of the rotor magnet to the core can urge the rotating assembly to move a flow regulating portion of the rotating assembly into engagement with a corresponding portion of the housing to block flow through the pumping chamber when the rotating assembly is at rest.

DRAWINGS

For a better understanding, reference may be made to the accompanying drawings.

FIGS. 3A and 3B are magnified views of portions of the ventricular assist device illustrating certain parts in different positions.

DESCRIPTION

Figure 1:
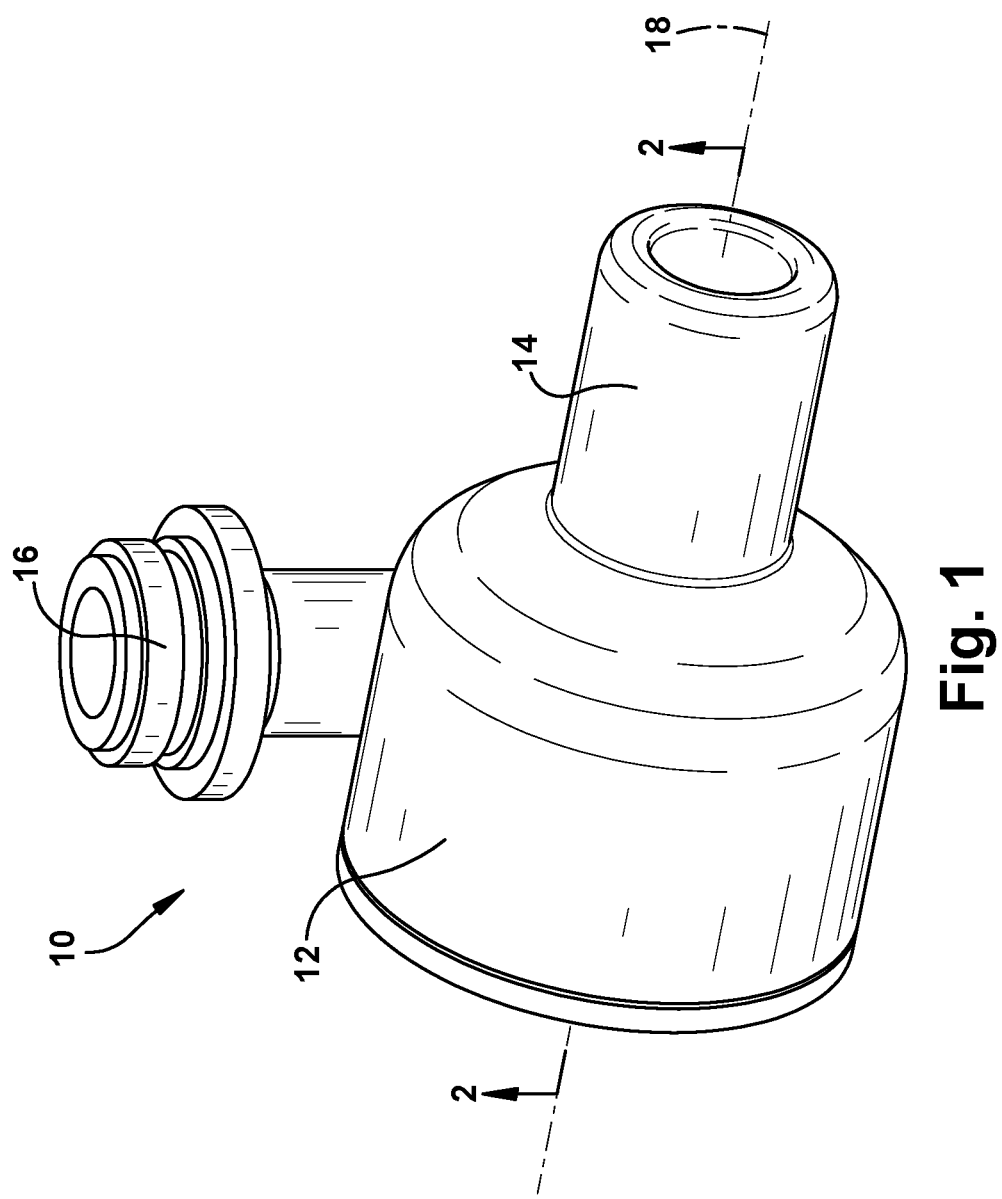
FIG. 1 is a perspective view of a ventricular assist device, according to an example configuration of the invention.
Figure 2:
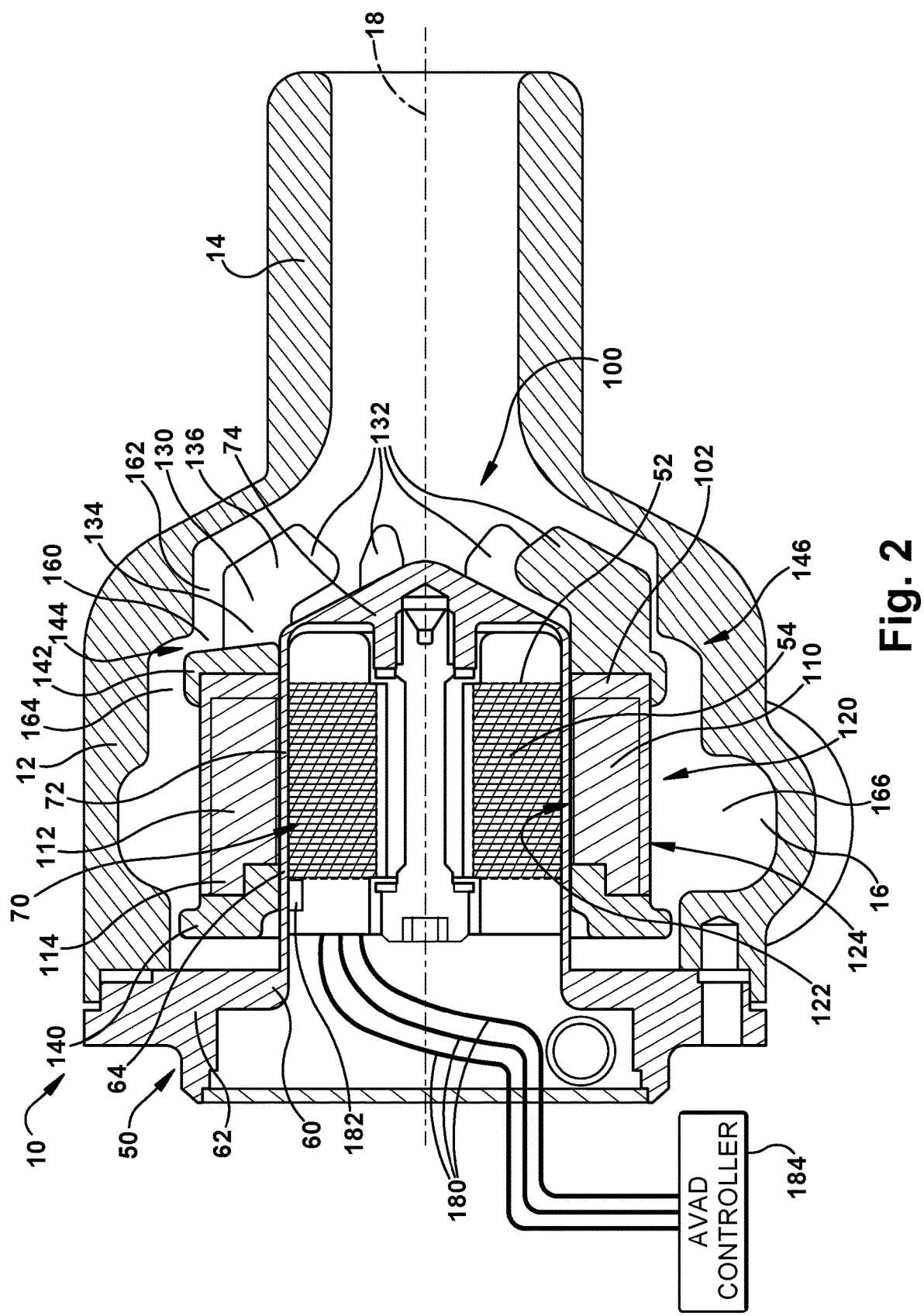
FIG. 2 is a sectional view of the ventricular assist device taken generally along line 2-2 in FIG. 1.

An example configuration of a ventricular assist device (VAD) 10 is illustrated in FIGS. 1-3. The VAD 10 is a permanently implantable brushless DC motor driven centrifugal pump that can be used as a left ventricular assist device (LVAD) or a right ventricular assist device (RVAD). The VAD 10 includes a pump housing 12 that has an inlet 14 and an outlet 16. The inlet 14 is aligned with a central pump axis 18 of the VAD 10. The VAD 10 also includes a stator assembly 50 and a rotating assembly 100, both of which are supported in the pump housing 12.

The stator assembly 50 includes a laminated stator core 52 upon which stator windings 54 are wound. In an example configuration, the core 52 includes ferromagnetic (e.g., steel) laminations upon which copper wire stator windings 54 are wound. The core 52 and windings 54 are supported in a stator housing 60, which encapsulates the core and windings, forming the outer structure of the stator assembly 50. The stator housing 60 includes a base portion 62 defining an annular flange that facilitates connecting the stator assembly 50 to the pump housing 12 by means, such as screws or threaded fasteners. The stator housing 60, particularly the base portion 62, creates a fluid-tight seal with the housing 12 due to lapping the mating surfaces flat. Additional sealing can be provided, for example, through the inclusion of O-rings, gaskets, sealant beads, etc.

The stator housing 60 also includes a stator enclosure 64 that encapsulates and surrounds the core 52 and windings 54. The stator enclosure 64, along with the core 52 and windings 54, help define a motor stator 70 of the VAD 10. The motor stator 70 is positioned within the pump housing 12 and extends axially along the pump axis 18. The stator enclosure 64 has a generally cylindrical outer wall 72 that terminates with a tapered or conical end portion 74 presented toward the pump inlet 14.

The rotating assembly 100 includes a rotor magnet 110 and a rotor enclosure 102 that encapsulates and surrounds the rotor magnet. The rotor enclosure 102 and the rotor magnet 110 help define a motor rotor 120 of the VAD 10. The rotor enclosure 102, rotor magnet 110, and thus the motor rotor 120 have a generally hollow cylindrical configuration with a cylindrical inner wall 122 and a generally cylindrical outer wall 124 between which the rotor magnet 110 is supported. The inner wall 122 of the motor rotor 120 has a diameter sufficient to form a clearance with the outer wall 72 of the motor stator 70.

The rotating assembly 100 also includes an impeller 130 connected to a terminal end of the rotor enclosure 102 and thus forms a terminal end of the motor rotor 120. The impeller 130 includes a plurality of radially extending impeller blades 132 that are spaced radially about the cylindrical end of the motor rotor 120. As shown in FIG. 2, each impeller blade 132 includes a base portion 134 that extends axially from the end of the rotor enclosure 102 and an angled portion 136 that extends at an angle from the base portion radially inward at an angle approximately equal to the taper angle of the conical end portion 74 of the motor stator 70. The impeller 130 thus can have an open configuration, omitting a back plate from which the impeller blades extend.

The rotating assembly 100 also includes a secondary impeller portion 140 that extends radially outward from the outer wall 124 at the end of the rotor enclosure 102 opposite the impeller 130. The rotating assembly 100 further includes an annular regulator rim portion 142 that extends radially outward from the outer wall 124 at the end of the rotor enclosure 102 opposite the secondary impeller 140 and adjacent the base of the impeller 130. The secondary impeller 140 and the regulator rim 142 define opposite ends of the rotor enclosure 102.

The materials used to construct the VAD 10 can be those materials conducive to blood pumping implementations. For example, portions of the VAD 10 that are exposed to blood flow during use, such as portions of the pump housing 12, the stator assembly 50, and the rotating assembly 100, can be formed from, coated, or encased in a biocompatible material, such as stainless steel, titanium, ceramics, polymeric materials, composite materials, or a combination of these materials. For example, portions of the stator assembly 50, such as the stator enclosure 64, and portions of the rotor assembly 100, such as the rotor enclosure 102, can be formed from stainless steel or titanium. As another example, the pump housing 12 and the impeller 130 can be formed of a polymeric or composite material. Additionally, surfaces or portions of the VAD 10 that may contact each other during use, such as the stator enclosure 64 and the rotor enclosure 102, can also be formed or coated with low friction materials, such as a fluorocarbon polymer coatings, diamond-like carbon coatings, ceramics, titanium, and diamond coated titanium.

The VAD housing 12 defines several internal portions of the VAD 10 between the inlet 14 and the outlet 16. A pumping chamber 160 is positioned adjacent the pump inlet 14 and extends from the pump inlet to a volute chamber 166 that includes the pump outlet 16. Between the inlet 14 and the volute chamber 166, the housing 12 is contoured so as to define axial portions of the pumping chamber 160 of varying diameter. Adjacent the inlet 14, the housing 12 tapers radially outward to define a first portion or chamber 162 of the pumping chamber 160 having a diameter that provides a clearance just greater than the outer diameter of the impeller 130. This first chamber 162 extends from the inlet 14 to the annular shoulder 80. Adjacent the annular shoulder 80, the housing 12 again tapers radially outward to define a second portion or chamber 164 of the pumping chamber 160 having a diameter greater than the first chamber 162. This second chamber 164 extends from the annular shoulder 80 to the volute chamber 166.

In an assembled condition of the VAD 10, the rotating assembly 100 is fitted onto the stator assembly 50, and the stator assembly is connected to the pump housing 12 as described above. In the assembled condition, the motor rotor 120 of the rotating assembly 50 is fitted onto the motor stator 70 of the stator assembly 50. The clearance between the inner wall 122 of the motor rotor 120 and the outer wall 72 of the motor stator 70 permits the rotating assembly 100 to rotate relative to the stator assembly 50 about the pump axis 18. This clearance also permits the rotating assembly 100 to move axially relative to the stator assembly 50 along the pump axis 18.

Axial movement of the rotating assembly 100 in one direction (to the left as viewed in FIG. 2) can be constrained due to engagement between the rotor enclosure 102, specifically the secondary impeller 140, and the base portion 62 of the stator housing 60. Axial movement of the rotating assembly 100 in the opposite direction (to the right as viewed in FIG. 2) can be constrained due to engagement between the rotor enclosure 102 and the stator housing 60. More specifically, in this opposite direction, axial movement of the rotating assembly 100 can be constrained due to engagement between the regulator rim 142 and an annular shoulder 80 of the pump housing 12.

A flow regulating aperture 144 is defined between the annular shoulder 80 and the regulator rim 142. The flow regulating aperture 144 opens when the rotating assembly 100 moves to the left as viewed in FIG. 2 and closes when the rotating assembly moves to the right as viewed in FIG. 2. An open condition of the flow regulating aperture is illustrated in FIG. 3A. A closed condition of the flow regulating aperture is illustrated in FIG. 3B.

The VAD 10 is configured so that axial movement of the rotating assembly 100 causes the impeller 130 to move between the first and second chambers 162 and 164 of the pumping chamber 160. Specifically, when the rotating assembly 100 moves to the left in FIG. 2, the impeller blades 132 are at least partially positioned in the second chamber 164. When the rotating assembly 100 moves to the right in FIG. 2 to the closed condition of the flow regulating aperture 144, the impeller blades 132 are positioned entirely in the first chamber 162. As the flow regulating aperture 144 opens, the impeller 130 moves into the second chamber 164.

In operation of the VAD 10, the motor stator 70 and the motor rotor 120 define a brushless DC motor 150 that is operable in a known manner to impart rotation to the impeller 130 to move fluid, i.e., blood, from the inlet 14 into and through the pumping chamber 160 to the volute chamber 166 and to the outlet 16. As the rotating assembly 100 rotates, blood located between the impeller blades 132 moves with the rotating blades and is forced through the pumping chamber 160 to the volute chamber 166 and to the outlet 16 due to centrifugal forces. Blood being discharged from the impeller 130 creates a pressure differential that draws additional blood into the impeller though the inlet 14. Circulation through the VAD 10 is thereby established.

The rotor magnet 110 has a first, main or motor portion 112 and a second, regulator portion 114. The motor portion 112 extends the majority of the length of the motor rotor 120 between the secondary impeller 140 and the regulator rim 142. The motor portion 112 has a substantial thickness, extending between the inner wall 122 and outer wall 124 of the rotor enclosure 102. Although the regulator portion 114 can contribute, it is the motor portion 112 that contributes the majority of the magnetic flux involved in creating the motive force of the electric motor 150. The regulator portion 114 is positioned at an end of the rotor magnet 110 opposite the impeller 130 and adjacent the secondary impeller 140. The regulator portion 114 has a thickness that is less than that of the motor portion 112, e.g., about half the width of the motor portion. The regulator portion 114 is also positioned radially farther, i.e., away from the motor stator 70.

The stator core 52 has an axial length that is greater than the axial length of the motor portion 112 of the rotor magnet 110. This contributes to the ability of the rotating assembly 100 to move axially within the pumping chamber 160 during pump operation with little or no impact to the motive force imparted by the motor 150. The mechanical constraints enforced by the engagement of the rotating assembly 100 with the stator assembly 50 at one end and with the pump housing 12 at the other end define the absolutes in terms of axial freedom of the rotating assembly. Within these mechanical constraints, the rotating assembly can be magnetically constrained by the electromagnetic forces created by the core 52 and the magnetic forces of the rotor magnet 110. The rotor magnet 110, and thus the rotating assembly 100, can travel freely in the axial direction within the length of the core 52. Travel beyond the core 52 causes the core to exert a magnetic axial pull on the rotor magnet 110 and, thus, the rotating assembly 100. Thus, through the configuration and arrangement of the core 52 and the rotor magnet 110 in the assembled condition of the VAD 10, the axial location beyond which magnetic constraints ensue can be selected to permit free axial travel within a certain range and prohibit axial travel beyond that range.

Advantageously, the VAD 10 can be configured so that axial movement of the rotating assembly 100 relative to the stator assembly 50 is magnetically constrained in one or both directions. Thus, the length and positioning of the core 52, the length of the rotor magnet 110, and the positioning of the rotor magnet within the rotating assembly 100 can be selected to determine which type of constraint, either magnetic or mechanical, are enforced at each end of axial travel. In the example configuration of FIG. 2, for instance, mechanical constraints can be enforced where the regulator rim 142 engages the annular shoulder 80 of the pump housing 12, and magnetic constraints can be forced at the opposite end of the rotating assembly 100 as the secondary impeller 140 approaches the base portion 62 of the stator assembly 50. In this instance, as the rotating assembly 100 moves axially to a position beyond which open the pumping aperture 144 opens fully, and the strong motor portion 112 of the rotor magnet 110 moves axially beyond the end of the stator core 52, a large magnetic restoring force builds and constrains the rotating assembly 100, which helps prevent the secondary impeller 140 from rubbing against the base portion 62 of the stator assembly.

The rotor magnet 110 is magnetically attracted to the steel laminations 52 of the stator core 52. The motor portion 112 of the rotor magnet 110, being comparatively axially long and radially thick, has a strong attraction to the stator core 52 when compared with the comparatively axially short and radially thin regulator portion 114. Additionally, the regulator portion 114 can be spaced radially from the core 52, leaving the motor portion 112 radially close to the core, which further magnifies the differential in their respective magnetic attractions to the core. The regulator portion 114 can extend axially beyond the stator core 52. Thus, while the motor portion 112 can be configured so as not to produce an axial pull on the rotating assembly 100, the regulator portion 114 does produce an axial pull on the rotating assembly. The relative size, spacing, configuration, and extent of the regulator portion 114 can be selected to provide the desired amount of axial pull on the rotating assembly 100.

This VAD 10 includes a flow regulating aperture 144 defined by the rotating assembly 100 and the pump housing 12. More specifically, the flow regulating aperture 144 is defined between the regulator rim 142 and the annular shoulder 80. During operation of the VAD 10, the rotating assembly 100 can move axially within the pumping chamber 160 between the axial constraints enforced by the secondary impeller 140 and the regulator rim 142. When the pump is at rest, the ferromagnetic attraction of the regulator portion 114 to the ferrous (steel) laminations in the core 52, combined with the regulator portion being offset/extending axially beyond the core, moves the rotating assembly to the right as viewed in FIG. 2 and as indicated generally by the arrow in FIG. 3B. When this occurs, the regulator rim 142 engages the annular shoulder 80, closing the flow regulating aperture 144.

From this, it will be appreciated that the VAD 10 includes a flow regulator 146 that includes the regulator rim 142, annular shoulder 80, and regulator portion 114 of the rotor magnet 110. The regulator portion 114 of the rotor magnet 110 can be configured and dimensioned such that the force with which the regulator portion holds the rotating assembly 100 in the closed condition of FIG. 3B can be overcome by hydrodynamic pumping forces produced when the VAD 10 is operated to circulate blood. The hydrodynamic pumping forces urge the rotating assembly 100 to move to place the flow regulating aperture 144 toward the open condition of FIG. 3A.

When the VAD 10 is operated, the hydrodynamic pumping forces created by operation of the impeller 130 in the blood oppose the magnetic forces of the regulator portion 114 and urge the rotating assembly 100 to the left as viewed in FIG. 2 and as indicated generally by the arrow in FIG. 3A. As these forces exceed the force with which the rotor magnet 110 maintains the flow regulating aperture 144 in the closed condition, the rotating assembly 100 moves, causing the regulator rim 142 to lift-off from the annular shoulder 80. This opens the flow regulating aperture 144, permitting blood to circulate through. When the VAD 10 is operated, blood is drawn in through the inlet 14 and into the first chamber 162. As the flow regulating aperture 144 opens, the blood enters the second chamber 164, passes into the volute chamber 166, and is discharged through the outlet 16.

Axial shuttling of the rotating assembly 100 during pump operation changes the size of the flow regulating aperture 144. Since pumped blood must pass through the flow regulating aperture 144, the volumetric flow rate of the blood pumped by the VAD 10 at a given pump speed is determined at least in part by the size of the flow regulating aperture, i.e., the axial position of the rotating assembly 100 in the pumping chamber 160. During operation of the VAD 10, the hydrodynamic pumping forces imposed by the impeller 130 balance with the magnetic forces imposed by the regulating portion 114 of the rotor magnet 110, and equilibrium will be achieved. This equilibrium can be characterized by the axial position of the rotating assembly 100 in the pumping chamber 160.

There are a variety of factors that can help determine the axial position of the rotating assembly 100 in the pumping chamber 160. For example, one factor affecting the axial position of the rotating assembly 100 is the speed at which the VAD 10 is operated. Pump speed has a great effect on the hydrodynamic pumping forces produced by the impeller 130. Pump speed therefore has a great effect on the degree to which the magnetic attraction of the regulator portion 114 is overcome, the axial position of the rotating assembly 100, and the degree to which the flow regulating aperture is open. All things being equal, lower pump speed would produce a smaller opening of the flow regulating aperture 144 and a correspondingly lower flow rate, and higher pump speed would produce a larger opening of the flow regulating aperture and a correspondingly higher flow rate.

Additionally, the physiology of the patient in which the VAD 10 is implanted can also help determine the axial position of the rotating assembly 100. Blood pressure differentials across the pump can affect the axial position response of the rotating assembly 100 at a given pump speed. For example, depending on the implementation of the VAD 10 (LVAD or RVAD), the systemic or pulmonary blood pressures seen at the pump outlet 16 can affect the axial position of the rotating assembly at a given pump speed. Advantageously, during operation of the VAD 10, the axial position of the rotating assembly 100 modulates along with the cardiac cycle, so that the aperture 144 opens with a surge in output at the start of systole (FIG. 3A) and closes during diastole, attenuating the output (FIG. 3B). In this way, the dynamic coupling of pump capacity is automatically and precisely timed to the action of the ventricle. In effect, the pump responds in kind with every heartbeat, which can allow a near physiologic-looking aortic pulse pressure and flow pulse of about 10 L/min (200% flow pulsatility) when in the LVAD mode.

At any time that the VAD 10 is not running, i.e., when the rotating assembly 100 is not rotating, the magnetic forces of the rotor magnet 110 take over and close the flow regulating aperture 144. Advantageously, when the VAD 10 is implanted in a patient, the regulator 146 regulates flow while the pump operates and also acts as a safety mechanism that blocks flow should, for example, power to the VAD 10 be lost. When the regulator 146 closes the flow regulating aperture 144, blood cannot backflow through the pump. This is important because, if the rotating assembly 100 stops and backflow occurs, not only is the VAD 10 not assisting the ventricle, it is actually working against the ventricle. The regulator 146 thus acts as an inherent backflow prevention valve.

Additionally, the regulator 146 allows for testing the patient's recovery by allowing the pump to be stopped while still implanted to see how the patient's heart responds. This can be done non-invasively simply by cutting power to the VAD 10. When power is cut, the regulator 146 closes the regulating aperture 144 and the patient's heart is on its own without any losses due to backflow, which can cause regurgitation within the ventricle. If the patient responds well, the pump can be removed via a surgical pump removal procedure. If the patient doesn't respond well, the VAD 10 can be re-started. The ability to wean a patient from the VAD 10 in this manner is particularly advantageous because there is no need for a surgical procedure to test whether the patient has recovered, as is the case with other ventricular assist devices.

As an additional feature, because the axial movement of the rotating assembly 100 is immediately responsive to the pump's hemodynamic environment, the patient's heart rate, timing and relative strength of ventricular contractions can be indicated by the combination of speed, power and future rotor position signals, all of which are available from the VAD controller 184.

The pump inlet is to be inserted into the native ventricle so that intraventricular pressure appears at the pump inlet. As the pump inlet pressure peaks during systole, the aperture is pushed further open allowing a momentary surge in pump output thereby amplifying pulsatility. This can be coupled with speed modulation to further amplify the pulsatility of the system. A rotor position sensor 182, such as a Hall sensor embedded in the motor stator or a coil positioned at the end of the stator windings that inductively senses the presence of the rotor magnet 110, can monitor the rotor magnet 110 position and can be used to create a speed control feedback loop via pump control wires 180. The control algorithm can be tuned to achieve maximum system pulsatility. Alternately, system inputs may be entered by the researcher or managing physician to create either a specified pulsatility or a pulsatility schedule that varies between co-pulsation and counter pulsation. In addition, waveform shape of the speed pulsatility can be varied to adjust hemodynamic characteristics.

The volute chamber 166 can be axially offset from the impeller 130, for example, in a manner similar or identical to that which is disclosed in U.S. Pat. No. 8,517,699, the disclosure of which is hereby incorporated by reference in its entirety. Since the volute section 166 is axially offset from the impeller 130, the impeller can operate over a wide range of flow/speed without driving adverse secondary flow patterns, allowing the VAD 10 to operate as either an LVAD at high speed (~3400 rpm), or an RVAD at low speed (~2600 rpm). The design intent would be to use it as either an LVAD or an RVAD without modification, and with the same electronic hardware.

The rotor position sensor 182 embedded in the stator 50 detects the axial position of the rotating assembly 100, which correlates to the pump pressure rise and pump speed. This information, in combination with speed and power data, would be used to calculate the calibrated pumped flow, allowing the device to act as a virtual flow meter.

The axial position signal provided by the Hall sensor 182 is immediately responsive to the hemodynamic environment of the pump. The VAD 10 can therefore offer real-time patient monitoring. Bench test and in vivo characterization of the VAD 10 can be used to establish characteristic relationships between the dynamic pump operating parameters created or seen by the VAD controller 184 (speed, power, and rotor axial position), and the hemodynamic environment of the pump characterized by the rotor axial position indicated by the Hall sensor 182. With characterization, these signals can then be used to estimate, in real time, the following parameters to control pump speed and to evaluate native ventricular function.

Beat rate can be determined as a function of rotor axial position frequency.

Pump mean flow can be determined as a function of speed, power, and rotor axial position.

Pump flow pulse amplitude can be determined as a function of speed, power pulse, and rotor axial position pulse.

Pump mean pressure rise can be determined as a function of speed, power, and rotor axial position.

Pump pressure pulse amplitude can be determined as a function of speed, power pulse, and rotor axial position pulse.

Pump mean work can be determined as a function of flow multiplied by pressure rise.

Pump pulse work can be determined as a function of beat rate, flow pulse, and pressure pulse.

Aortic valve opening/closing can be determined as a function of an identifying feature in the rotor axial position wave form or via a power vs. position hysteresis loop.

Suction recognition can be determined as a function of an identifying feature in rotor axial position wave form or via a power vs. position hysteresis loop.

Relative change in pulsatility since baseline can be determined as a function of a comparison with the history of hemodynamic parameters.

These hemodynamic parameters form the basis for a continuous patient monitor that would reside within the VAD controller 184, be ambulatory with the patient, and could inform managing physicians of a change in patient condition without the use of invasive pressure monitoring or other equipment. The patient monitor could be interrogated through the VAD system interface, or remotely by telemetric means.

The VAD 10 and the system in which the VAD is implemented, i.e., the VAD and the VAD controller 184, can possess various capabilities that heretofore were unavailable with the current state of the art in ventricular assist device technology. Examples of these capabilities include:

The ability to maintain physiological pulsatility in patients on VAD support. Reinforcing the native pressure and flow pulsatility by dynamically coupling with the native ventricle will create a near-physiological aortic pulse pressure without pump speed modulation. The VAD can also use speed modulation to further enhance pulsatility. Physiological pulsatility may reduce complications, such as gastrointestinal bleeding and will also allow conventional, noninvasive blood pressure measurement.

The ability to reduce the risk of pump thrombosis or hemolysis by eliminating problematic features (e.g., inlet/outlet stator vanes and pivot bearings) and offer full passive suspension of the rotor. Passive suspension (opposing magnetic pull with hydrodynamic pumping forces) is simple compared to active magnetic levitation, which is complex and has a potential for failure.

The ability to prevent backflow by enabling automatic flow shutoff in the event of pump stoppage.

The ability to provide noninvasive evaluation of pump weanability by automatic flow shutoff. Automatic shut-off will also allow a pump-off test without blood regurgitation or the need to occlude the outflow graft.

The ability to operate across a wide range of operating specifications, enabling use of the VAD as either an LVAD or RVAD with the same pump hardware and electronics.

The ability to avoid suction events by automatically attenuating pump output through automatic aperture closure.

Figure 4A:
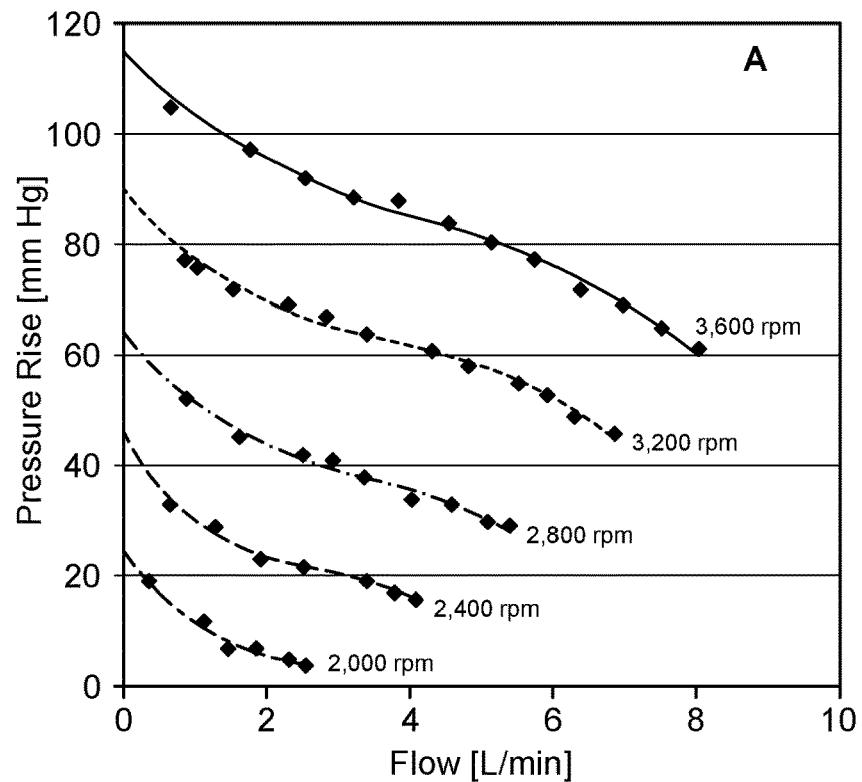
FIGS. 4A and 4B are charts illustrating performance characteristics of the ventricular assist device.
Figure 4B:
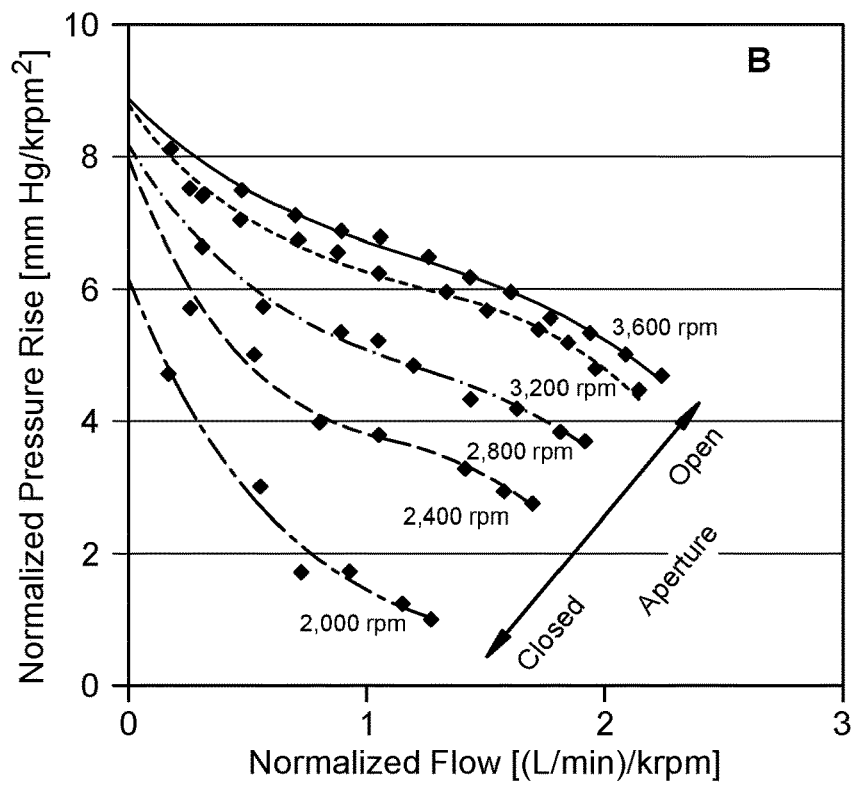

Bench testing was performed on a static mock loop to obtain pressure-flow curves at various pump speeds (FIG. 4A). To obtain normalized pressure-flow curves, flow is normalized by dividing by speed, and pressure is normalized by dividing by speed squared (FIG. 4B). If the pump geometry does not change with varying pump speeds, i.e., without a regulated pumping aperture, the normalized pressure-flow curves should align along a single curve. In the case of the VAD 10, however, the regulator 146 closes the regulating aperture 144 with lower pump speed, which decreases pump performance. Therefore, due to the regulator 146 structure implemented in the VAD 10, normalized pressure-flow curves do not lie along a single curve but vary based on pump speed (FIG. 4B). Due to this unique feature, the VAD 10 can be used as an LVAD or RVAD using the same identical pump design, simply by adjusting pump speed.

While aspects of the ventricular assist device have been particularly shown and described with reference to the preferred embodiment above, it will be understood by those of ordinary skill in the art that various additional embodiments may be contemplated without departing from the spirit and scope of the disclosed embodiments. Other aspects, objects, and advantages can be obtained from a study of the drawings, the disclosure, and the appended claims.

We claim:

1. A ventricular assist device having a centrifugal pump configuration, the ventricular assist device comprising:
   a housing comprising a pumping chamber;
   a stator assembly supported in the housing, the stator assembly comprising a core having a length measured along a pump axis; and
   a rotating assembly supported in the housing and rotatable relative to the stator assembly about the pump axis, the rotating assembly comprising an impeller positioned in the pumping chamber and a rotor magnet, the rotating assembly engaging the housing and blocking flow through the pumping chamber when the pump is at rest.

2. The ventricular assist device recited in claim 1, wherein the rotating assembly is movable axially along the pump axis relative to the pump housing and the stator assembly, and wherein the rotating assembly and stator assembly are configured and arranged such that the magnetic attraction of the rotor magnet to the core urges the rotating assembly to move axially relative to the stator assembly such that flow through the pumping chamber is blocked when a flow regulating portion of the rotating assembly engages with a corresponding portion of the housing.

3. The ventricular assist device recited in claim 2, wherein the rotor magnet comprises a first portion having a comparatively strong magnetic attraction to the core and that does not influence the axial position of the rotating assembly relative to the stator, and a second portion having a comparatively weak magnetic attraction to the core and that does influence the axial position of the rotating assembly relative to the stator.

4. The ventricular assist device recited in claim 2, wherein the rotor magnet comprises a first portion and a second portion, wherein the rotating assembly and stator assembly are configured and arranged such that the first portion of the rotor magnet is positioned between axial ends of the core during pump operation, and the second portion of the rotor magnet is at least partially positioned axially beyond an axial end of the core regardless of the axial position of the rotating assembly relative to the stator assembly.

5. The ventricular assist device recited in claim 2, wherein the rotor magnet has a hollow cylindrical structure, the first portion of the rotor magnet having a first thickness and the second portion of the rotor magnet having a second thickness that is less than the first thickness.

6. The ventricular assist device recited in claim 5, wherein the first thickness and second thickness are measured between respective cylindrical inner and outer walls of the first and second portions of the rotor magnet, and wherein the inner wall of the second portion of the rotor magnet is spaced radially farther from the core than the first portion of the rotor magnet.

7. The ventricular assist device recited in claim 2, further comprising a flow regulating aperture defined by the pump housing and the rotating assembly, wherein the flow regulating aperture has a size that varies with the axial position of the rotating assembly relative to the stator assembly.

8. The ventricular assist device recited in claim 7, wherein the flow regulating aperture is defined between the flow regulating portion of the rotating assembly and the corresponding portion of the housing.

9. The ventricular assist device recited in claim 8, wherein the flow regulating portion of the rotating assembly comprises an annular rim adjacent the impeller.

10. The ventricular assist device recited in claim 7, wherein the impeller is configured to move fluid from a pump inlet through the pumping chamber to a pump outlet, and wherein the flow regulating aperture is configured to regulate flow through the pumping chamber.

11. The ventricular assist device recited in claim 7, wherein the rotating assembly is configured such that hydrodynamic pumping forces created by the impeller urge the rotating assembly to move axially relative to the stator assembly in a direction that increases the size of the flow regulating aperture.

12. The ventricular assist device recited in claim 11, wherein the impeller and pumping chamber are configured so that the pump geometry changes in response to the axial position of the of the impeller in the pumping chamber so that pump output increases in response to increases in the size of the flow regulating aperture.

13. The ventricular assist device recited in claim 2, wherein the rotating assembly is configured such that hydrodynamic pumping forces created by the impeller urge the rotating assembly to move axially relative to the stator assembly in a direction that is opposite the axial direction that the rotor magnet urges the rotating assembly to move.

14. The ventricular assist device recited in claim 13, wherein the impeller and pumping chamber are configured so that the pump geometry changes in response to the axial position of the of the impeller in the pumping chamber so that pump output varies in response to the axial position of the rotating assembly.

15. The ventricular assist device recited in claim 2, wherein the impeller and pumping chamber are configured so that the pump geometry changes in response to the axial position of the of the impeller in the pumping chamber so that pump output varies in response to the axial position of the rotating assembly.

16. The ventricular assist device recited in claim 15, wherein the axial position of the rotating assembly changes in response to differential pressures across the pump so that the axial position of the rotating assembly follows the cyclic pressure changes produced by the native ventricle for which it is implemented to assist.

17. The ventricular assist device recited in claim 16, wherein the pump output is configured to increase in response to systole and decrease in response to diastole.

18. The ventricular assist device recited in claim 2, further comprising a sensor for providing a signal indicative of the axial position of the rotating assembly relative to the housing and a controller for determining via calibration the hemodynamic environment of the pump in response to the sensed axial position of the rotor assembly and motor operating parameters for the ventricular assist device.

19. The ventricular assist device recited in claim 18, wherein the hemodynamic environment of the pump determined by the controller via calibration is characterized by at least one of the following parameters:
  beat rate determined as a function of rotor axial position frequency;
  mean flow determined as a function of speed, power, and rotor axial position;
  pump flow pulse amplitude determined as a function of speed, power pulse, and rotor axial position pulse;
  pump mean pressure rise determined as a function of speed, power, and rotor axial position;
  pump pressure pulse amplitude determined as a function of speed, power pulse, and rotor axial position pulse;
  pump mean work determined as a function of flow multiplied by pressure rise;
  pump pulse work determined as a function of beat rate, flow pulse, and pressure pulse;
  aortic valve opening/closing determined as a function of an identifying feature in the rotor axial position wave form or via a power versus position hysteresis loop;
  suction recognition determined as a function of an identifying feature in rotor axial position wave form or via a power versus position hysteresis loop; and
  relative change in pulsatility since baseline determined as a function of a comparison with the history of hemodynamic parameters.

20. The ventricular assist device recited in claim 2, wherein the pump is configured to block back flow through the pumping chamber in response to a loss of electrical power to the pump.

21. A ventricular assist device having a centrifugal pump configuration, the ventricular assist device comprising:
  a housing comprising a pumping chamber;
  a stator assembly supported in the housing, the stator assembly comprising a stator core;
  a rotating assembly supported in the housing, the rotating assembly being rotatable relative to the stator assembly about the pump axis and movable relative to the stator assembly along the pump axis, the rotating assembly comprising an impeller positioned in the pumping chamber and a rotor magnet;
  wherein the magnetic attraction of the rotor magnet to the core urges the rotating assembly to move axially in a first direction, and hydrodynamic pumping forces created by the impeller during pump operation urge the rotating assembly to move axially in a second direction, opposite the first direction;
  wherein the pumping chamber and the impeller are configured so that pump output decreases when the rotating assembly moves axially in the first direction and increases when the rotating assembly moves axially in the first direction; and
  wherein the axial position of the rotating assembly responds inherently to differential pressures across the pump and variations in pump speed by moving to an axial position where the hydrodynamic forces produced by impeller rotation balance with magnetic forces urging the rotating assembly in the opposite direction.

22. The ventricular assist device recited in claim 21, wherein the magnetic attraction of the rotor magnet to the core urges the rotating assembly to move a flow regulating portion of the rotating assembly into engagement with a corresponding portion of the housing to block flow through the pumping chamber when the rotating assembly is at rest.

* * * * *